United States Patent [19]

Burke et al.

[11] Patent Number: 5,630,999

[45] Date of Patent: *May 20, 1997

[54] ORAL COMPOSITION CONTAINING ANIONIC SURFACTANTS HAVING REDUCED ADVERSE REACTION TO ORAL TISSUE

[75] Inventors: Michael R. Burke, Somerset, N.J.; Spencer Holover, Grenada, Grenada

[73] Assignee: Colgate Palmolive Company, New York, N.Y.

[*] Notice: The portion of the term of this patent subsequent to Mar. 22, 2011, has been disclaimed.

[21] Appl. No.: 185,531

[22] Filed: Jan. 21, 1994

Related U.S. Application Data

[63] Continuation-in-part of Ser. No. 78,527, Jun. 16, 1993, Pat. No. 5,296,215.

[51] Int. Cl.$^6$ .............................. C22C 38/42; A61K 31/70
[52] U.S. Cl. .................... 424/49; 424/52; 424/54; 514/25; 514/115
[58] Field of Search ................... 424/49, 52, 54; 514/25, 115

[56] References Cited

U.S. PATENT DOCUMENTS

| | | | |
|---|---|---|---|
| 3,832,460 | 8/1974 | Kosti | 424/54 |
| 3,989,827 | 11/1976 | Apostolatos et al. | 424/235 |
| 4,568,540 | 2/1986 | Asano et al. | 424/52 |
| 4,748,158 | 5/1988 | Biermann et al. | 514/25 |
| 5,109,127 | 4/1992 | Sekiguchi et al. | 536/115 |
| 5,296,215 | 3/1994 | Burke et al. | 424/49 |

FOREIGN PATENT DOCUMENTS

| | | |
|---|---|---|
| 9212701 | 8/1992 | European Pat. Off. . |
| 9307249 | 4/1993 | European Pat. Off. . |

OTHER PUBLICATIONS

JP Patent Abstract of Japan vol. 16 No. 461 (C–988), 25 Sep. 1992 & JP A, 04 164020 (Lion Corp.).

*Primary Examiner*—Elli Peselev
*Attorney, Agent, or Firm*—Paul Shapiro

[57] ABSTRACT

An oral composition exhibiting reduced irritability to oral tissue is disclosed wherein the composition contains a surfactant system comprised of a combination of an anionic surfactant such as sodium lauryl sulfate and a $C_{12}$–$C_{22}$ alkyl glycoside.

24 Claims, No Drawings

ORAL COMPOSITION CONTAINING ANIONIC SURFACTANTS HAVING REDUCED ADVERSE REACTION TO ORAL TISSUE

This application is a continuation-in-part of Ser. No. 08/078,527 filed Jun. 16, 1993, now U.S. Pat. No. 5,296,215.

BACKGROUND OF THE INVENTION

1. Field of the Invention

This invention relates generally to an oral composition containing an anionic surfactant which exhibits reduced adverse reaction to oral tissue.

2. The Prior Art

Surfactants, and particularly anionic surfactants such as sodium lauryl sulfate are an essential ingredient of oral compositions and serve as a solubilizing, dispersing, emulsifying and wetting agent for the other ingredients present in the dentifrice and is especially effective in solubilizing the flavor present. A cosmetic effect of the presence of the surfactant is that it promotes foaming of the oral composition. Oral compositions with strong foaming ability are preferred by consumers since the foaming provides the perception that the oral composition cleans effectively only if it foams well.

The incorporation of anionic surfactants such as sodium lauryl sulfate in oral compositions such as dentifrices is known to cause adverse reactions to oral tissue such adverse reactions being reported in R. C. Caldwell and R. E. Stallard, *A Textbook of Preventive Dentistry*, 196, W. B. Saunders (1977); L. J. Guarnieri, IADR, Abstract No. 661 (1974); L. J. Guarnieri, *Thesis*, University of Indiana (1970). One example of such adverse reaction is gingival irritation.

The art therefore has been seeking means to reduce the adverse reaction to oral tissue caused by oral compositions containing an anionic surfactant such as sodium lauryl sulfate.

SUMMARY OF THE INVENTION

It has unexpectedly been discovered that oral compositions such as dentifrices, gels mouthwashes and the like containing anionic surfactants such as sodium lauryl sulfate are less irritating to oral tissue when an effective amount of an alkyl glycoside is incorporated in the oral composition.

In copending patent application U.S. Ser. No. 08/078,527 there is disclosed an oral composition having improved organoleptic properties and rheological storage stability, the oral composition containing a surfactant system comprised of a mixture of purified sodium lauryl sulfoacetate and an alkyl glycoside. There is no indication in the application that the inclusion of an alkyl glycoside would be effective in reducing the irritancy of anionic surfactants such as sodium lauryl sulfate.

DESCRIPTION OF THE PREFERRED EMBODIMENTS

Suitable examples of anionic surfactants used in the preparation of the oral compositions of the present invention include water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate, higher alkyl sulfates such as sodium lauryl sulfate, alkyl aryl sulfonates such as sodium dodecyl benzene sulfonate, higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

The anionic surfactant is incorporated in the oral composition of the present invention at a concentration of about 0.1 to about 3.0% by weight and preferably about 0.3 to about 1.5% by weight.

The inclusion of an alkyl glycoside in oral compositions containing anionic surfactants decreases the irritancy of the anionic surfactant without deleteriously affecting the foam properties of the oral composition.

Alkyl glycosides which are incorporated in the oral compositions of the present invention have the formula

$RO(C_6H_{10}O_5)_xH$ wherein R is an aliphatic residue of a $C_{12}$–22 fatty alcohol and x is an integer from 1 to 20, and preferably 1 to 10 and most preferably 1.2 to 2.0.

The incorporation of alkyl glycosides in oral compositions are known to the art. For example, U.S. Pat. No. 4,748,158 discloses the use of alkyl glycosides in combination with an antimicrobial biguanide compound to improve antimicrobial performance. U.S. Pat. No. 4,923,685 discloses an antimicrobial mouthwash containing an antimicrobial biguanide compound, a flavorant and as a surfactant system, a combination of a $C_8$–$C_{14}$ alkyl glycoside and an ethoxylated fatty acid glyceride and sorbitan partial ester.

Alkyl glycosides used in the practice of the present invention are typically produced by reacting glucose or an oligosaccharide with a fatty alcohol containing 12–22 carbon atoms and more preferably with alcohols containing an alkyl group having 12 to 18 carbon atoms. Alkyl glycosides having an alkyl group of 12–16 carbon atoms are preferred in the practice of the present invention. Alkyl glycosides prepared using fatty alcohols containing less than 12 carbon atoms suffer from the presence of lower alkyl chain, e.g., $C_4$–$C_{10}$ free alcohol impurities which deleteriously effect the organoleptic properties of the oral care compositions into which the alkyl polyglycoside is incorporated. Polyglycosides containing $C_{12}$–$C_{16}$ alkyl glycosides are available commercially from Horizon Chemical Division of Henkel, Inc under the trademark "Plantaren".

An especially preferred Plantaren glycoside useful in the practice of the present invention is a non-ionic alkyl polyglycoside sold under the trademark Planteren 1200 UP characterized by the formula:

$C_nH_{2n+1}O(C_6H_{10}O_5)_xH$ wherein n=12–16 and x(degree of polymerization)=1.4. The product has a pH of 11.4; a specific gravity at 25° C. of 1.1 gms/ml; a calculated HLB of about 11.5 and a Brookfield viscosity at 35° C., 21 spindle, 5–10 RPM of about 15,000 to about 20,000 centistokes per second.

The alkyl glycoside is incorporated in the oral care compositions of the present invention at a concentration of about 0.1 to about 2.0% by weight and preferably about 0.2 to about 1.0% by weight. In preparing a surfactant system in accordance with the present invention, the anionic surfactant and alkyl glycoside are present in the oral composition at a weight ratio of anionic surfactant to polyglycoside of 10:1 to 1:5, a weight ratio of 3:1 to 1:1 being preferred.

The oral compositions of the present invention may be substantially semi-solid or pasty in character, such as a toothpaste, gel or dental cream. The vehicle of such semi-solid or pasty oral preparations generally contains a polishing material.

Examples of materials useful as polishing agents in the oral composition of the present invention include sodium bicarbonate, water-insoluble siliceous polishing agents, hydrated alumina and dicalcium phosphate, including dicalcium phosphate dihydrate and anhydrous dicalcium phosphate dihydrate and anhydrous dicalcium phosphate. Siliceous polishing agents include colloidal silica xerogel, precipitated silica and sodium alumniosilicates or silica grades containing combined alumina, typically in amount of about 0.1–7% by weight. Other polishing materials include insoluble sodium metaphosphate, calcium carbonate, trimagnesium phosphate, magnesium carbonate, etc. Mixtures of polishing agents may be used.

Typically, the polishing material is included in semi-solid or pasty dentifrice compositions of the present invention in an amount of from about 15 to about 60% by weight and preferably from about 20 to about 55%.

In toothpaste, gel or dental creams, the oral composition is formulated using a water and humectant carrier typically in an amount ranging from about 10 to about 90% of the composition.

Humectant carriers such as sorbitol, typically commercially available in 70% aqueous solution, glycerine, low molecular weight polyethylene glycol (e.g. about 200 to 600) or propylene glycol exemplify humectant carriers used to formulate the toothpaste, gel or dental compositions and are incorporated in the oral compositions of the present invention at a concentration of about 10 to about 40% by weight and preferably about 15 to about 30% by weight.

Toothpastes, creams and gels typically contain a natural or synthetic thickener or gelling agent in concentrations of about 0.1 to about 10% by weight preferably about 0.5 to about 5 weight %. Suitable thickeners include Irish moss, gum tragacanth, starch, hydroxyethylpropylcellulose, hydroxybutyl methyl cellulose, hydroxypropyl methyl cellulose, hydroxyethyl cellulose and sodium carboxymethyl cellulose.

The oral compositions of the present invention also include products which are substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70% to about 99.9% by weight of the preparation.

The pH of the oral compositions of the present invention is generally in the range of from about 6 to about 8.0. The pH can be controlled with acid (e.g., citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

In certain preferred forms of this invention, fluorine-providing salts having anti-caries efficacy may be incorporated in the oral compositions and are characterized by their ability to release fluoride ions in water. Among these materials are inorganic metal salts, for example, sodium fluoride, potassium fluoride, cuprous fluoride, stannous fluoride, sodium flurosilicate, ammonium fluorosilicate, sodium monofluorophosphate, alumina mono-and difluorophosphate.

The amount of the fluoride-providing compound is dependent to some extent upon the type of compound, its solubility, and the type of oral preparation, but it must be a nontoxic amount, generally about 0.01 to about 3.0% in the composition. In a semi-solid or pasty oral composition such as a gel, toothpaste or cream, an amount of such compound may be used, but it is preferable to employ sufficient fluoride compound to release about 0.005% to 1%, more preferably about 0.1% of fluoride ion. Typically, in the cases of the alkali metal fluorides this component is present in an amount up to about 2.5% by weight, based on the weight of the preparation, and preferably in the range of about 0.05% to 1%. In the case of sodium monofluorophosphate, the compound may be present in an amount of about 0.1–3.0%

In a liquid oral preparation such as a mouthwash or rinse, the fluoride-providing compound is typically present in an amount sufficient to release up to about 1.0%, preferably about 0.001% to 0.5% by weight of fluoride ion. Generally, about 0.01 to about 3.0 wt. % of such compound is present.

Pyrophosphate salts having anti-tartar efficacy such as a dialkali or tetra-alkali metal phosphate salts such as $Na_4P_2O_7$, $K_4P_2O_7$, $Na_2K_2P_2O_7$, $Na_2H_2P_2O_7$ and $K_2H_2P_2O_7$, long chain polyphosphates such as sodium hexametaphosphate and cyclic phosphate such as sodium trimetaphosphate are incorporated in solid oral compositions of the present invention preferably at a concentration of about 0.5 to about 8.0% by weight. In liquid oral preparations, the pyrophosphate salts are incorporated at a concentration of about 0.1 to about 3% by weight.

Antibacterial agents may also be included in the oral compositions of the present invention. Especially useful are non-cationic antibacterial agents which are based on phenolic and bisphenolic compounds, halogenated diphenyl ether, halogenated salicylanilides and particularly fluro salicylanilides, benzoate esters and carbanilides. Examples of such compounds are 4-chlorophenol, 2,2'-trichloro-2-hydroxy-diphenyl ether (Triclosan), 3,4'5 trichlorosalicylanilide, 5-n-octanoyl-3'-trifluoromethyl salicylanilide, esters of p-hydroxybenzoic acid, especially methyl, ethyl, propyl, butyl and benzyl esters, 3,4,4'-trichlorocarbanilide and 3,3',4-trichlorocarbanilide. Triclosan and 5-n-octanoyl-3'-trifluromethyl salicylanilide in amounts ranging from 0.03% to 1% are preferred for use in the compositions of the present invention. A nonionic antimicrobial agent such as a sesquiterpene alcohol such as merolidol and bisabolol is also useful in the present invention.

When antibacterial agents are included in the oral compositions of the present invention, an antibacterial enhancing agent may also be included in the oral composition. The use of antibacterial enhancing agents in combination with antibacterial agents such as Triclosan and halogenated salicylanilide is known to the art, as for example U.S. Pat. No. 5,188,821 and U.S. Pat. No. 5,192,531. Preferably, the antibacterial enhancing agent is a natural or synthetic anionic polymeric polycarboxylate having a molecular weight of about 1,000 to about 1,000,000, preferably about 30,000 to about 500,000. The synthetic anionic polymeric polycarboxylates are generally employed in the form of their free acids or preferably partially or more preferably fully neutralized water soluble alkali metal e.g., potassium and preferably sodium or ammonium salts. Preferred are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 500,000. These copolymers are available, for example, as Gantrez, e.g. AN 139 (M.W. 500,000), AN 119 (M.W. 250,000); and preferably S-97 Pharmaceutical Grade (M.W. 70,000), of GAF Corporation.

Polysiloxanes such as liquid silicone oils such as diphenyl or di ($C_1$–$C_4$) alkyl polysiloxanes and particularly dimethylpolysiloxane, may also be employed in the practice of the present invention as an antibacterial enhancing agent.

The antibacterial enhancing agent is incorporated in the compositions of the present invention in weight amounts of about 0.05 to about 5%, and preferably about 0.1 to about 3%.

Any suitable flavoring or sweetening material may also be employed. Examples of suitable flavoring constituents are flavoring oils, e.g. oil of spearmint, peppermint, wintergreen, sassafras, clove, sage, eucalyptus, cinnamon, lemon, and orange, and methyl salicylate. Suitable sweetening agents include sucrose, lactose, maltose, xylitol, sodium cyclamate, perillartine, aspartyl phenyl alanine, methyl ester, saccharine and the like. Suitably, the flavor and sweetening agents may each or together comprise from about 0.1% to 5% more of the preparation.

Agents used to diminish teeth sensitivity such as strontium chloride, potassium nitrate and potassium citrate can also be included in the oral compositions of the present invention at concentrations of about 0.1% to about 10% by weight.

Various other materials may be incorporated in the oral compositions of this invention such as preservatives, such as sodium benzoate, silicones, chlorophyll compounds and/or ammoniated material such as urea, diammonium phosphate, and mixtures thereof. These adjuvants, where present, are incorporated in the preparations in amounts which do not substantially adversely affect the properties and characterstics desired.

Tooth whitening agents may also be included in the oral compositions of the present invention. Especially useful are oxidizing agents such as hydrogen peroxide, urea peroxide, peracetic acid, calcium peroxide, sodium perborate, sodium percarbonate or any other source that, in aqueous solutions, acts as an hydrogen peroxide source. The amount of active oxygen in such oral compositions can vary from 0.7% to 5% by weight and preferably about 0.5% to about 2% by weight.

The oral composition of the present invention may be prepared by suitably mixing the ingredients. In the preparation of the semi-solid or pasty composition such as a toothpaste, a thickener such as carboxymethyl cellulose or hydroxyethyl cellulose is dispersed with a humectant, water, salts such as tetrasodium pyrophosphate, sodium fluoride or sodium monofluorophosphate, and sweetener such as saccharin are then added and mixed. A polishing agent such as dicalcium phosphate dihydrate, anionic surfactant, alkyl glycoside, and flavor are then added. The ingredients are then mixed under vacuum for about 15–30 minutes. The resulting gel or paste is then tubed.

The following examples are further illustrative of the present invention, but it is understood that the invention is not limited thereto. All amounts and proportions referred to herein and in the appended claims are by weight unless otherwise indicated.

EXAMPLE I

A series of toothpastes was prepared having the compositions listed in Table I, in which the surfactant system was comprised of a surfactant system containing 1.3% by weight (on an active's dry weight basis) of anionic surfactant and an alkyl glycoside.

TABLE I

| INGREDIENT | COMPOSITION WEIGHT % |||||||
|---|---|---|---|---|---|---|---|
| | A | B | C | D | E | F | G |
| Dicalcium phosphate dihydrate | 48.00 | 48.00 | 48.00 | 48.00 | 48.00 | 48.00 | 48.00 |
| Glycerin | 22.22 | 22.22 | 22.22 | 22.22 | 22.22 | 22.00 | 22.00 |
| Anionic Surfactant | 1.01 | 1.06 | 1.03 | 1.22 | 1.07 | 1.19 | 1.19 |
| $C_{12}$–$C_{16}$ alkyl glycoside* (AG) | 0.65 | 0.65 | 0.65 | 0.65 | 0.65 | 0.65 | 0.65 |
| Flavor | 0.95 | 0.95 | .95 | .95 | .95 | .95 | .95 |
| Sodium monofluorophosphate (MFP) | 0.76 | 0.76 | .76 | .76 | .76 | .76 | .76 |
| Na Carboxymethyl cellulose (NaCMC) | 0.50 | 0.50 | 0.50 | 0.50 | 0.50 | 0.50 | 0.50 |
| Hydroxyethyl Cellulose (HEC) | 0.50 | 0.50 | 0.50 | 0.50 | 0.50 | 0.50 | 0.50 |
| Tetrasodium pyrophosphate (TSPP) | 0.25 | 0.25 | 0.25 | 0.25 | 0.25 | 0.25 | 0.25 |
| Na Saccharin | 0.20 | 0.20 | 0.20 | 0.20 | 0.20 | 0.20 | 0.20 |
| Deionized water pH 6.6–7.2 | q.s. | q.s. | q.s. | q.s. | q.s. | q.s. | q.s. |

The anionic surfactant used in each of the above compositions A–F is listed below:

| Composition | Anionic Surfactant | Active Ingredient (%) |
|---|---|---|
| A | Sodium lauryl sulfate | 97 |
| B | Sodium alkyl benezene sulfonate | 92 |
| C | Sodium lauroyl sarcosinate | 95 |
| D | Sulfocolaurate | 80 |
| E | Sodium N-methyl N-cocoyl taurate | 97 |
| F | Sodium cocomono glyceride sulfate | 82 |
| G | Dodecyl sodium sulfoacetate | 82 |

*Analysis of alkyl glucoside (Planteran 1200 UP):
Activity, %         48–52
Free alcohol, %     0.4–0.8
Average D.P.        1.4
pH, 10% sol.        11.4–11.8

The composition was prepared by mixing glycerin together with NaCMC and HEC, then adding TSPP and Na Saccharin, followed by deionized water. The mixture was placed in a double planetary vacuum mixer. Dicalcium phosphate dihydrate, MFP, flavor, the anionic surfactant and AG were added to the mixture, and the ingredients mixed under vacuum for about 15–20 minutes. Homogeneous pastes were obtained using compositions A–F The irritancy of the anionic surfactant/alkyl glycoside combination used to prepare the toothpaste compositions A–F of the present invention was evaluated in accordance with the test procedure disclosed in an article entitled "Predicting Surfactant Irritation from the Swelling Response of a Collagen Film," J. Soc. Cosmet, Chem. 37, 199–210 (July/August, 1986). In this in vitro test, the swelling (tritiated water uptake) of a collagen film substrate correlates with the irritation of anionic surfactants and products based on these ingredients. Swelling response is concentration dependent and higher substrate swelling indicates greater irritation potential. The results of this in vitro test have been found to correlate with findings from established in vitro and in vivo laboratory and clinical assessments.

In performing the irritancy test, collagen film supplied by Colla-Tec Inc., Plainsboro, N.J., was prepared from bovine deep flexor tendon and cut into 2.54×2.54 cm (1×1 inch) squares, approximately 20 mg by weight. Each square was placed in a 20-ml screw cap vial and treated with a 5 ml solution containing a mixture of 1.68 mM anionic surfactant (AS) in combination with the 0.3% alkyl glucoside (AG) Planteran 1200 and enough tritiated ($^3H_2O$) water to give $3 \times 10^5$ dpm/ml.

The film squares were removed from all the solutions, and each rinsed in 2 liters of deionized water for about 5 seconds to remove any adhering tritiated water, and thereafter placed in a liquid scintillation vial.

The films exposed to the surfactant solutions were digested in the vials with 1 ml 2N NaOH and dissolved in Ecolume (ICN Biomedicals, Inc.) scintillation cocktail, acidified with 0.35 ml concentrated perchloric acid, and analyzed for radioactivity using a Beckman LS06800 scintillation spectrometer. The swelling was defined as microliters tritiated water taken up per milligram dry collagen (μl/mg). The results are recorded in Table II below.

For purposes of comparison, the irritancy test was repeated with the exception that the irritancy of a surfactant system consisting solely of the anionic surfactant at the same concentration as the anionic surfactant/alkyl glucoside system was also determined. The results of these comparative tests are also recorded in Table II below.

TABLE II

| Anionic Surfactant (AS) | AS | AS + 0.3% AG |
|---|---|---|
| | | Irritancy - Collagen Swelling (ul/mg) |
| Sodium lauryl Sulfate | 23.738 | 14.633 |
| Sodium alkyl benezene sulfonate | 15.197 | 9.773 |
| Sodium lauroyl sarcosinate | 9.872 | 7.127 |
| Sulfocolaurate | 9.685 | 9.204 |
| Sodium N-methyl N-cocoyl taurate | 8.872 | 7.927 |
| Sodium cocomono glyceride sulfate | 7.785 | 6.647 |
| Sodium Lauryl sulfoacetate | 7.618 | 7.048 |

The results recorded in Table II indicate that in every instance the anionic surfactant/alkyl glycoside system was substantially less irritating than when the anionic surfactant was present at the same concentration in the test solutions.

EXAMPLE III

To assess the foaming properties of the toothpastes containing the combination of an anionic surfactant and an alkyl glucoside in accordance with the present invention an artificial saliva solution was prepared following the procedure disclosed in Tavss et al J. Pharm. Sci, 1984, 73(g), 1148–52 having the composition shown below

| Composition of Artificial Saliva | |
|---|---|
| Ingredient | Concentration (g/l) |
| $CaCl_2.2H_2O$ | 0.228 |
| $MgCl_2.6H_2O$ | 0.061 |
| NaCl | 1.017 |
| $K_2CO_3.15H_2O$ | 0.603 |
| $NaH_2PO_4.H_2O$ | 0.204 |
| $Na_2HPO_4.7H_2O$ | 0.273 |
| Water | q.s. |
| Conc. HCl | sufficient to achieve pH 6.9 |

To the artificial saliva was added 16% by weight dicalcium phosphate dihydrate and 0.3% by weight flavoring agent along with a surfactant system consisting of an anionic surfactant and alkyl polyglucoside at varying weight ratios, which are shown in Table III. The anionic surfactants were sodium lauryl sulfate (SLS) Dodecyl Sodium Sulfoacetate (DSS) sodium N-methyl cocoyl taurate (SMCT) and sodium alkyl benzene sulfonate (SABS). The concentrations of the resulting test solution correspond to a 1:5 dilution of toothpaste in saliva, which is closely associated with toothpaste in the oral cavity.

In performing the foam test, fifteen ml of the test solution were transferred to a 50 ml sterile centrifuge tube. Six replicates were placed in a 37° C. water bath for approximately 15 minutes. The centrifuge tubes were clamped on to a Burrell Wrist-Action Shaker and were shaken an average of 50 times over a 10 second period. The tubes were displaced over 7.0 cm in each cycle. Upper and lower foam levels were recorded on the tubes between 5 and 20 seconds after shaking. The difference in the levels provided a "foam volume" value in milliliters. Increasing foam values correlate to increasing foamability perceived by consumers using the toothpaste.

A close correlation has been found to exist between the foam test results using diluted toothpaste and the foamability rated by a human test panel brushing with undiluted toothpaste. The foam volume of the test solutions is recorded in Table III below.

For purposes of comparison, the procedure of Example III was repeated except solutions were prepared wherein the anionic surfactant was the sole surfactant (0.03% by wt) or alkyl glycoside (0.03 wt. %). These comparative solutions were also tested for foamability. The foam values of these comparative solutions are also recorded in Table III.

TABLE III

| | Toothpaste Foamability | | | | | |
|---|---|---|---|---|---|---|
| Surfactant | Foam Volume (ml) AS/AG at Wt Ratio | | | | Foam Volume (ml) Individual Surfactant | |
| System | 1:3* | 1:1** | 3:1** | 10:1** | AS | AG |
| SLS/AG | 15 | 21 | 27 | 10 | 7 | 5 |
| DSS/AG | 25 | 25 | 27 | 25 | 25 | 5 |
| SMCT/AG | 21 | 22 | 21 | 20 | 20 | 5 |
| SABS/AG | 18 | 22 | 22 | 20 | 17 | 5 |

*AG = 0.03 wt. %, AS = 0.01 wt. %
**AS = 0.03 wt. %, AG varies

The data in Table III show that the oral compositions containing the anionic surfactant (AS)/alkyl glycoside (AG) surfactant systems exhibited foaming levels equal to or greater than the either anionic surfactant or alkyl glucoside alone.

What is claimed is:

1. An oral composition having a reduced irritancy to oral tissue the composition containing a surfactant system comprised of an effective amount of an anionic surfactant and an alkyl glycoside having the formula $RO(C_6H_{10}O_5)_xH$, wherein R is an aliphatic residue of a $C_{12}$ to $C_{22}$ fatty alcohol and x is an integer from 1 to 20.

2. The composition of claim 1 wherein the alkyl glycoside is characterized by R being an aliphatic residue of a $C_{12}$ to $C_{16}$ fatty alcohol and x is an integer from 1.2 to 2.0.

3. The composition of claim 2 wherein x in the formula is 1.4.

4. The composition of claim 1 wherein the anionic surfactant is sodium lauryl sulfate.

5. The composition of claim 1 wherein the anionic surfactant is sodium alkyl benzene sulfonate.

6. The composition of claim 1 wherein the anionic surfactant is sodium lauroyl sarcosinate.

7. The composition of claim 1 wherein the anionic surfactant is sulfocolaurate.

8. The composition of claim 1 wherein the anionic surfactant is sodium N-methyl-N-cocoyl taurate.

9. The composition of claim 1 wherein the anionic surfactant is sodium cocomoglyceride sulfate.

10. The composition of claim 1 wherein the anionic surfactant is sodium lauryl sulfoacetate.

11. The composition of claim 1 wherein the anionic surfactant is present in the oral composition at a concentration of about 0.1% to about 3.0% by weight and the alkyl glycoside is present in the oral composition at a concentration of 0.1% to 2.0%.

12. The composition of claim 1 wherein the weight ratio of anionic surfactant to glycoside is from 10:1 to 1:5.

13. A method for preparing a composition containing an anionic surfactant which exhibits reduced irritancy to oral tissue when applied in the oral cavity which method comprises preparing the oral composition containing the anionic surfactant and incorporating therein an effective amount of an alkyl glycoside having the formula $RO(C_6H_{10}O_5)xH$, wherein R is an aliphatic residue of an $C_{12}$ to $C_{22}$ fatty alcohol and x is an integer from 1 to 20.

14. The method of claim 13 wherein the alkyl glycoside is characterized by R being an aliphatic residue of a $C_{12}$ to $C_{16}$ fatty alcohol and x is an integer from 1.2 to 2.0.

15. The method of claim 14 wherein x in the formula is 1.4.

16. The method of claim 13 wherein the anionic surfactant is sodium lauryl sulfate.

17. The method of claim 13 wherein the anionic surfactant is sodium alkyl benzene sulfonate.

18. The method of claim 13 wherein the anionic surfactant is sodium lauroyl sarcosinate.

19. The method of claim 13 wherein the anionic surfactant is sulfocolaurate.

20. The method of claim 13 wherein the anionic surfactant is sodium N-methyl-N-cocoyl taurate.

21. The method of claim 13 wherein the anionic surfactant is sodium cocomoglyceride sulfate.

22. The method of claim 13 wherein the anionic surfactant is sodium lauryl sulfoacetate.

23. The method of claim 13 wherein the anionic surfactant is present in the oral composition at a concentration of about 0.1% to about 3.0% by weight and the alkyl glycoside is present in the oral composition at a concentration of 0.1% to 2.0%.

24. The method of claim 13 wherein the weight ratio of anionic surfactant to glycoside is from 10:1 to 1:5.

* * * * *